(12) United States Patent  (10) Patent No.: US 9,395,499 B2
Huang et al.  (45) Date of Patent: Jul. 19, 2016

(54) OPTICAL FIBER CONNECTOR, OPTICAL FIBER ADAPTOR AND OPTICAL FIBER CONNECTOR ASSEMBLY

(71) Applicant: Huawei Technologies Co., Ltd., Shenzhen (CN)

(72) Inventors: Xuesong Huang, Shenzhen (CN); Wenxin Wu, Shenzhen (CN); Shangjun Peng, Shenzhen (CN); Wei Zhang, Wuhan (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 120 days.

(21) Appl. No.: 14/186,776

(22) Filed: Feb. 21, 2014

(65) Prior Publication Data

US 2015/0260924 A1 Sep. 17, 2015

Related U.S. Application Data

(63) Continuation of application No. PCT/CN2012/077556, filed on Jun. 26, 2012.

(51) Int. Cl.
*G02B 6/38* (2006.01)

(52) U.S. Cl.
CPC .............. *G02B 6/3851* (2013.01); *G02B 6/389* (2013.01); *G02B 6/3821* (2013.01); *G02B 6/3825* (2013.01); *G02B 6/3849* (2013.01); *G02B 6/3869* (2013.01); *G02B 6/3891* (2013.01); *G02B 6/3893* (2013.01)

(58) Field of Classification Search
CPC ..... G02B 6/389; G02B 6/3891; G02B 6/3851
See application file for complete search history.

(56) References Cited

U.S. PATENT DOCUMENTS

| 4,595,251 A | 6/1986 | Moulin |
| 5,210,810 A | 5/1993 | Darden et al. |
| 6,371,660 B1 | 4/2002 | Roehrs et al. |
| 6,398,422 B1 | 6/2002 | Szilagyi et al. |
| 7,234,877 B2 * | 6/2007 | Sedor .................. G02B 6/3879 385/59 |

(Continued)

FOREIGN PATENT DOCUMENTS

| CN | 1333471 A | 1/2002 |
| CN | 101299085 A | 11/2008 |

(Continued)

OTHER PUBLICATIONS

Chinese Search Report received in Application No. 201280000748.0, mailed Jun. 26, 2012, 3 pages.

(Continued)

*Primary Examiner* — Omar R Rojas
(74) *Attorney, Agent, or Firm* — Slater Matsil, LLP

(57) ABSTRACT

Embodiments of the present invention provide an optical fiber connector assembly, an optical fiber adapter, and an optical fiber connector to solve the problem of inconvenience in use caused by using a thread-locking manner in the prior art. The optical fiber connector, optical fiber adapter and optical fiber connector assembly provided in the present invention may be used as an outdoor connector to achieve plug and play. The optical fiber connector supports blind-mate, and the operation is convenient. Time taken to install and disassemble the optical fiber connector provided in the present invention is only one-fifth of the time taken to install and disassemble a common thread connector.

9 Claims, 10 Drawing Sheets

(56) References Cited

U.S. PATENT DOCUMENTS

| | | |
|---|---|---|
| 7,467,896 B2 | 12/2008 | Melton et al. |
| 7,614,799 B2 | 11/2009 | Bradley et al. |
| 7,708,469 B2 | 5/2010 | Liu et al. |
| 8,465,311 B2 * | 6/2013 | Takamatsu ............ G02B 6/3821 439/247 |
| 2001/0038584 A1 | 11/2001 | Saito |
| 2005/0141817 A1 | 6/2005 | Yazaki et al. |
| 2006/0045430 A1 | 3/2006 | Theuerkorn et al. |
| 2009/0148104 A1 | 6/2009 | Lu et al. |
| 2010/0092137 A1 | 4/2010 | Niiyama et al. |
| 2010/0215322 A1 | 8/2010 | Matsumoto et al. |
| 2011/0038584 A1 | 2/2011 | Hyakutake |
| 2011/0211792 A1 | 9/2011 | Koreeda et al. |
| 2012/0071019 A1 | 3/2012 | Takamatsu |

FOREIGN PATENT DOCUMENTS

| | | |
|---|---|---|
| CN | 201689192 U | 12/2010 |
| CN | 102007437 A | 4/2011 |
| CN | 102012547 A | 4/2011 |
| CN | 2011215544 A | 10/2011 |
| CN | 102401941 A | 4/2012 |
| CN | 102870023 A | 1/2013 |
| DE | 102008019757 A1 | 10/2009 |
| EP | 0297439 A2 | 6/1988 |
| EP | 2431777 A1 | 3/2012 |
| GB | 1483688 | 8/1977 |
| GB | 2154333 A | 9/1985 |
| JP | 5171150 B2 | 6/1976 |
| JP | 04505813 A | 10/1992 |
| JP | 2005512148 A | 4/2005 |
| JP | 2006126845 A | 5/2006 |
| JP | 2010197854 A | 9/2010 |
| WO | 9015350 A1 | 12/1990 |
| WO | 03050579 A2 | 6/2003 |
| WO | 2008114830 A1 | 9/2008 |
| WO | 2009131993 A1 | 10/2009 |

OTHER PUBLICATIONS

Chinese Office Action received in Application No. 201280000748.0, mailed Nov. 5, 2013, 7 pages.

International Search Report received in Application No. PCT/CN2012/077556, mailed Feb. 28, 2013, 13 pages.

Extended European Search Report, Application No. 12879599.4, Applicant: Huawei Technologies Co., Ltd., dated May 9, 2014, 9 pages.

* cited by examiner

OPTICAL FIBER CONNECTOR, OPTICAL FIBER ADAPTOR AND OPTICAL FIBER CONNECTOR ASSEMBLY

This application is a continuation of International Application No. PCT/CN2012/077556, filed on Jun. 26, 2012, which is hereby incorporated by reference in its entirety.

TECHNICAL FIELD

The present invention relates to the field of computer telecommunications, and in particular, to an optical fiber adapter, and an optical fiber connector, optical fiber connector assembly.

BACKGROUND

An existing outdoor optical fiber connector generally uses a single thread-locking manner for a locking an optical fiber connector assembly when an optical fiber connector and an optical adapter engaged and to be locked each other. However, the optical fiber connector assembly has no additional locking structure, and therefore needs to be rotated multiple turns during locking and unlocking, thereby causing inconvenience in use.

SUMMARY OF THE INVENTION

A technical problem to be solved by embodiments of the present invention is to provide an optical fiber connector assembly, an optical fiber adapter, and an optical fiber connector to solve the problem of inconvenience in use caused by using a thread-locking manner in the prior art.

An embodiment of the present invention provides an optical fiber connector assembly, which includes a ferrule and an optical fiber. The ferrule is sleeved on the optical fiber. The optical fiber connector assembly includes an inner jacket element, an elastic element, and an outer jacket element. The inner jacket element is sleeved on one end of the ferrule. One end of the elastic element leans against one end of the inner jacket element adjacent to the ferrule. The outer jacket element is sleeved on the inner jacket element and the ferrule. One end of the outer jacket element is slideably connected to the inner jacket element and leans against an other end of the elastic element. The elastic element is configured to provide an elastic force to the outer jacket element in a direction away from the ferrule. An inner wall of an other end of the outer jacket element is provided with a bump. The ferrule includes a buckling elastic piece. The buckling elastic piece is fixed to one end of the ferrule away from the inner jacket element and the buckling elastic piece extends towards the inner jacket element.

An optical fiber adapter includes a socket formed with an optical fiber slot and two protection key slots. The optical fiber slot and the two protection key slots extend along an axial direction of the socket. The optical fiber slot is formed with a notch. The two protection key slots are located on two sides of the optical fiber slot. A periphery of the socket is formed with a second chute. The second chute is of a spiral shape. The second chute extends from one end of the socket along a axial direction of the socket. An end of extension of the second chute is bent towards one end of the socket.

An optical fiber connector includes an optical fiber connector assembly and an optical fiber adapter that matches the optical fiber connector assembly. The optical fiber connector assembly comprises a ferrule, an optical fiber, an inner jacket element, an elastic element, and an outer jacket element. The ferrule is sleeved on the optical fiber. The inner jacket element is sleeved on one end of the ferrule. One end of the elastic element leans against one end of the inner jacket element adjacent to the ferrule. The outer jacket element is sleeved on the inner jacket element and the ferrule. One end of the outer jacket element is slideably connected to the inner jacket element and leans against an other end of the elastic element. The elastic element is configured to provide an elastic force to the outer jacket element in a direction away from the ferrule. An inner wall of an other end of the outer jacket element is provided with a bump. The ferrule includes a buckling elastic piece. The buckling elastic piece is fixed to one end of the ferrule away from the inner jacket element and the buckling elastic piece extends towards the inner jacket element. The optical fiber adapter includes a socket, which is formed with an optical fiber slot and two protection key slots. The optical fiber slot and the two protection key slots extend along an axial direction of the socket. The optical fiber slot is formed with a second notch, where the second notch matches the buckling elastic piece. The two protection key slots are located on two sides of the optical fiber slot, which matches the ferrule. The optical fiber connector assembly further comprises protection keys. The protection key slots matches the protection keys. A periphery of the socket is formed with a second chute, which matches the bump. The second chute is of a spiral shape, and extends from one end of the socket along a axial direction of the socket, and a rear end of extension of the second chute latch the bump.

The optical fiber connector provided in the present invention may be used as an outdoor connector to achieve plug and play. The optical fiber connector supports blind-mate, and the operation is convenient. The time taken to install and disassemble the optical fiber connector is only one-fifth of the time taken to install and disassemble a common thread connector.

BRIEF DESCRIPTION OF THE DRAWINGS

To illustrate the technical solutions in the embodiments of the present invention more clearly, the following briefly introduces the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

DETAILED DESCRIPTION OF ILLUSTRATIVE EMBODIMENTS

The following clearly describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

An optical fiber connector assembly provided by an embodiment of the present invention implements simple and fast locking through a bump and a chute.

Figure 1:
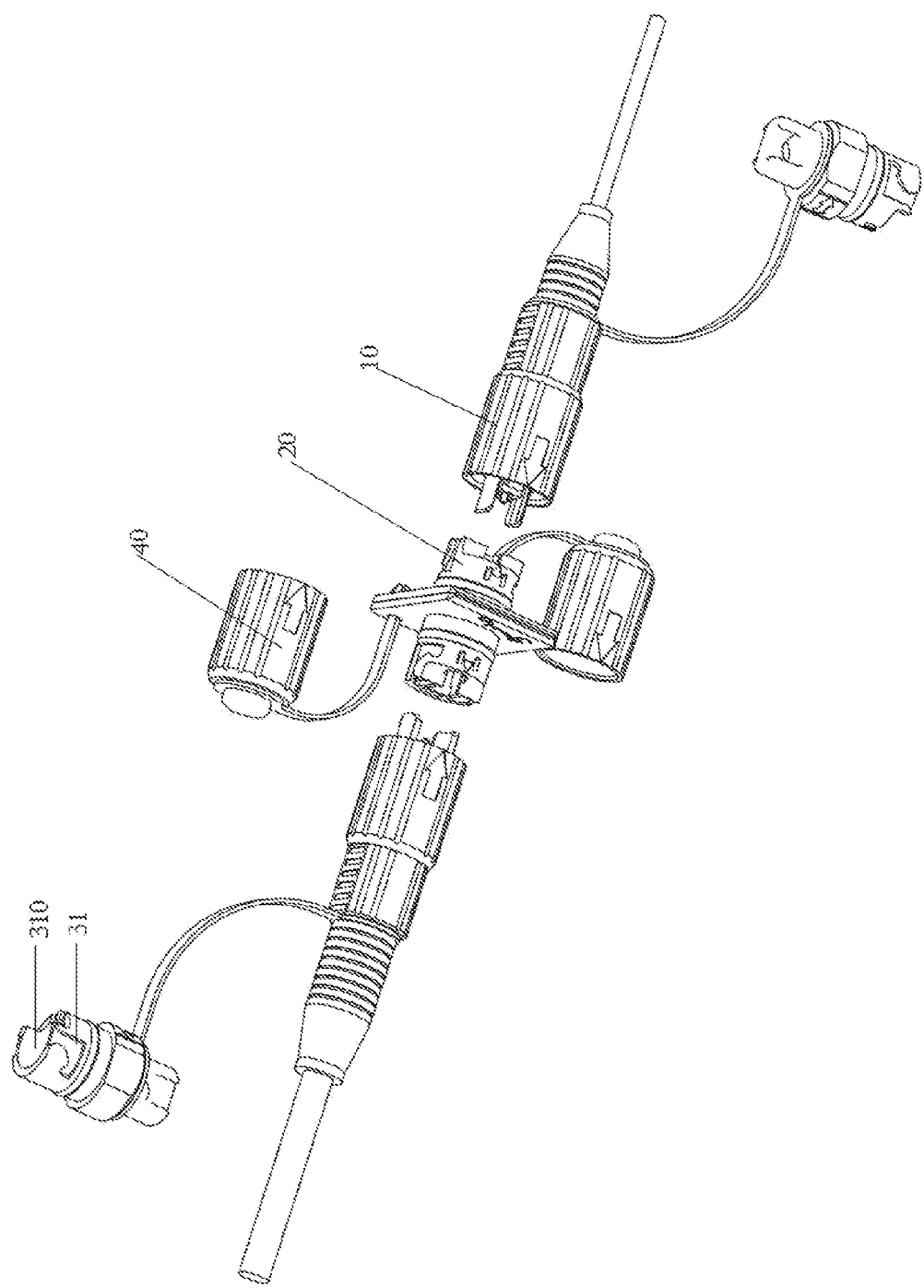
FIG. 1 is a schematic view of an optical fiber connector provided in the present invention.

Referring to FIG. 1, an embodiment of the present invention provides an optical fiber connector 100. The optical fiber connector 100 includes an optical fiber connector assembly 10 and an optical fiber adapter 20 matching the optical fiber connector assembly 10.

Figure 2:
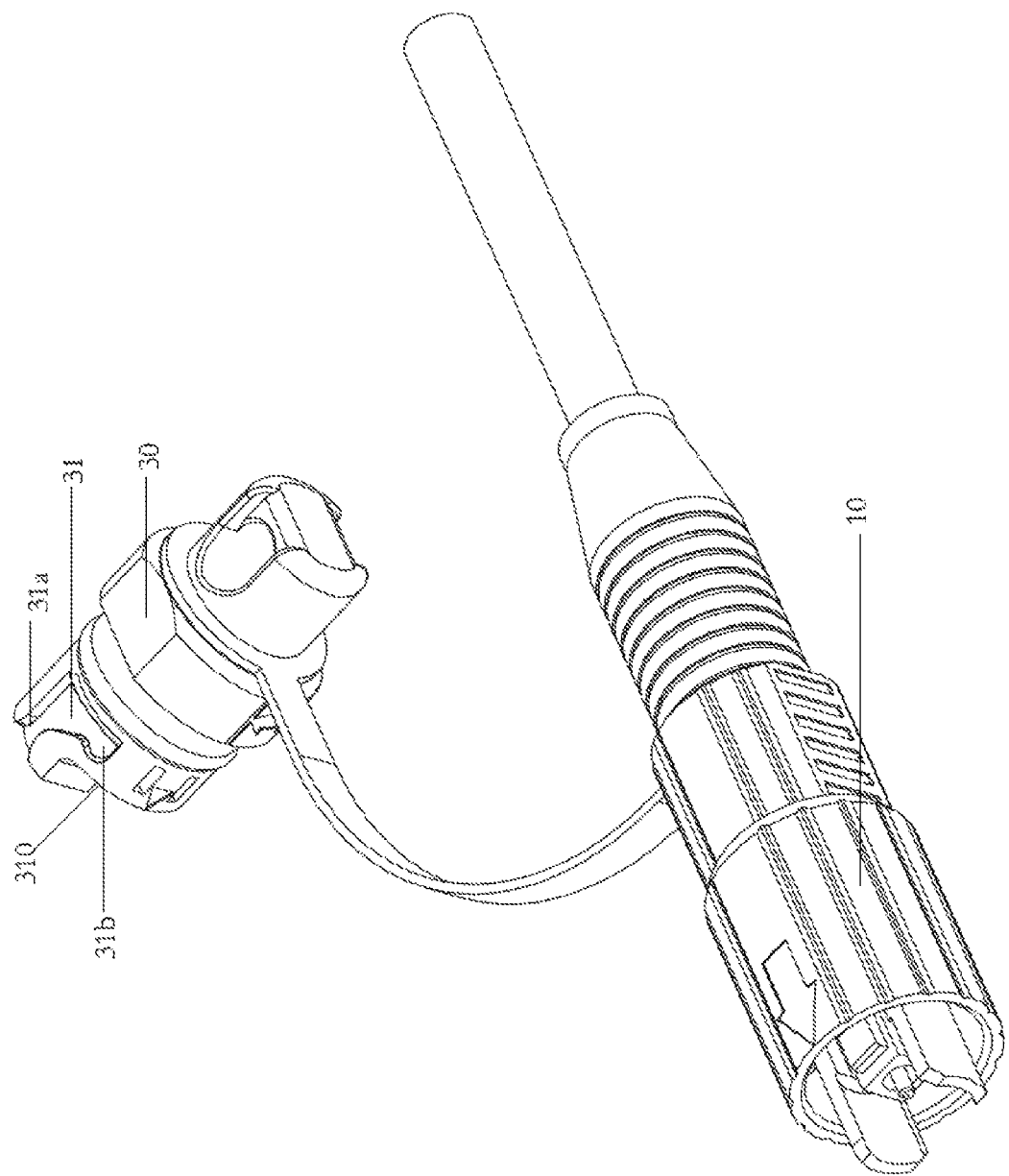
FIG. 2 is a schematic view of an optical fiber connector assembly of the optical fiber connector in FIG. 1.
Figure 3:
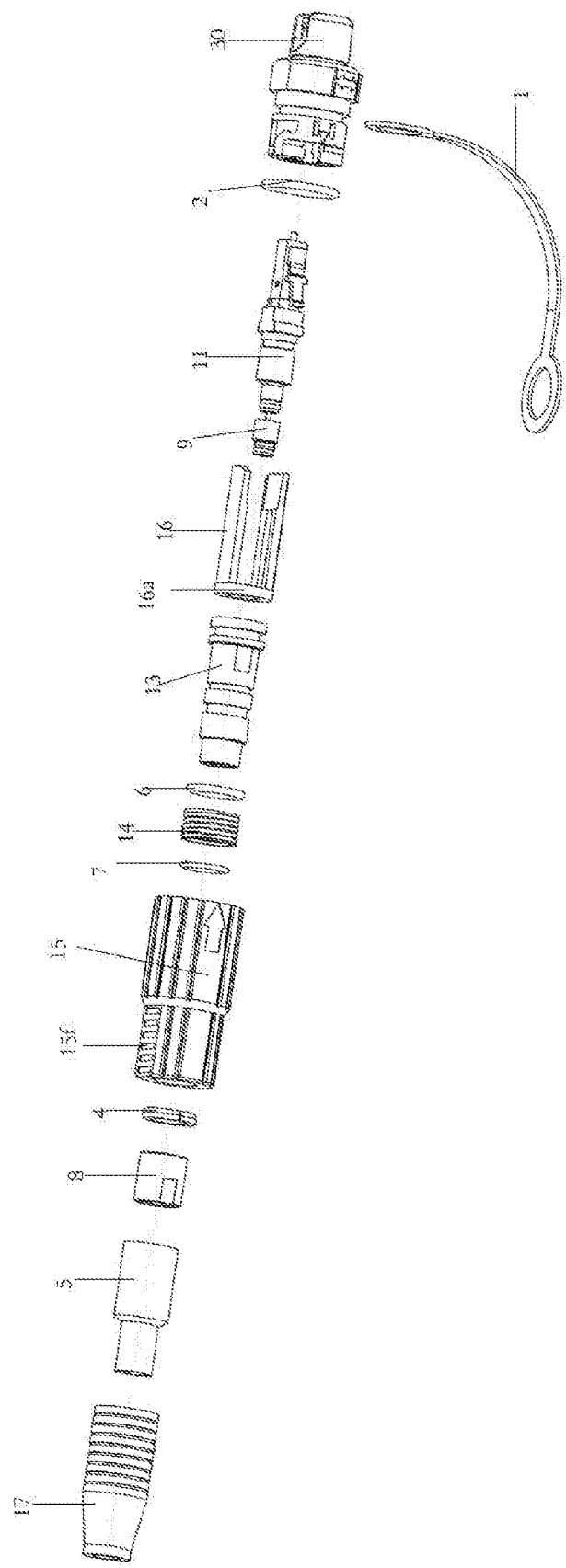
FIG. 3 is an exploded view of the optical fiber connector assembly in FIG. 2.
Figure 4:
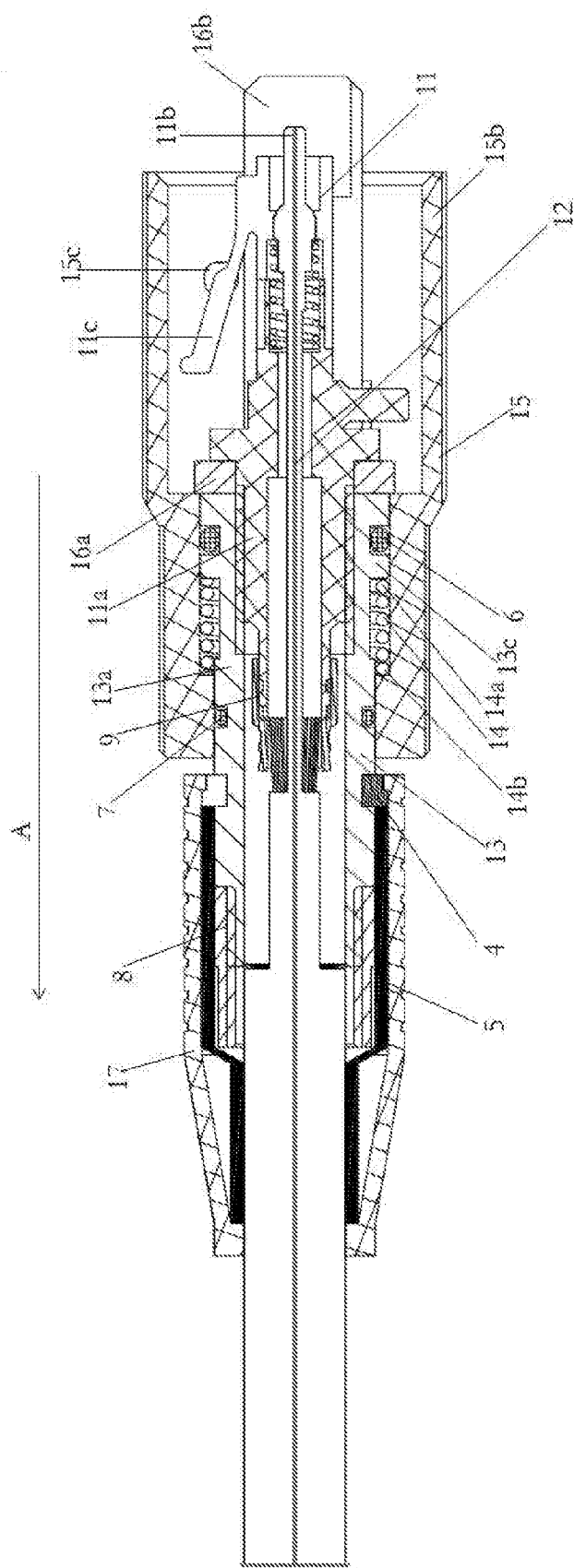
FIG. 4 is a schematic view of the inside of the optical fiber connector assembly in FIG. 2.

Referring to FIG. 2 to FIG. 4, the optical fiber connector assembly 10 includes a ferrule 11, an optical fiber 12, an inner jacket element 13, an elastic element 14, an outer jacket element 15, two protection keys 16 and a rear retainer 17. The ferrule 11, the inner jacket element 13, the elastic element 14, and the outer jacket element 15 are sleeved on the optical fiber 12 sequentially.

The ferrule 11 is sleeved on the optical fiber 12. In this implementation manner, the ferrule 11 is of a cylinder shape with a plurality of steps. The optical fiber 12 penetrates the ferrule 11. The ferrule 11 has two ends 11a and 11b disposed opposite to each other and the optical fiber 12 protrudes from the end 11b of the ferrule 11 that is away from the inner jacket element 13. The inner jacket element 13 is sleeved on the end 11a of the ferrule 11. The ferrule 11 includes a buckling elastic piece 11c, where the buckling elastic piece 11c is fixed to the end 11b of the ferrule 11 that is away from the inner jacket element 13 and the buckling elastic piece 11c extends towards the inner jacket element 13. Inner aramid filament yarn of the optical fiber 12 is riveted to the end 11a of the ferrule 11 by using a rivet ring 9.

The inner jacket element 13 includes two ends 13a and 13b disposed opposite to each other. The end 13a of the inner jacket element 13 is screwed to the end 11b of the ferrule 11. The other end 13b of the inner jacket element 13 is locked together with outer aramid filament yarn of the optical fiber 12 by using a nut 8. Riveting using the rivet ring 9 and locking using the nut 8 can increase tensile strength of the optical fiber connector assembly 10. The end 13a of the inner jacket element 13 is sleeved with O-shaped seal ring 7 and O-shaped seal ring 6 with a sealing function. The end 13a of the inner jacket element 13 includes a shaft shoulder 13c. The shaft shoulder 13c is configured to lean against the elastic element 14.

The elastic element 14 includes two ends 14a and 14b disposed opposite to each other. The end 14a of the elastic element 14 leans against the end 13a of the inner jacket element 13 that is adjacent to the ferrule 11. In this implementation manner, the elastic element 14 is a spring and the elastic element 14 is sleeved on the inner jacket element 13. The end 14a of the elastic element 14 leans against the shaft shoulder 13c of the inner jacket element 13.

The outer jacket element 15 includes two ends 15a and 15b disposed opposite to each other. The outer jacket element 15 is sleeved on the inner jacket element 13 and the ferrule 11, where the end 15a of the outer jacket element 15 is slideably connected to the inner jacket element 13 and leans against the other end 14b of the elastic element 14; the elastic element 14 is configured to provide an elastic force to the outer jacket element 15 in a direction away from the ferrule 11 (direction A), to protect against connection loosing. An inner wall of the other end 15b of the outer jacket element has a bump 15c disposed.

In this implementation manner, the outer jacket element 15 is a cylinder with a plurality of step bores. The end 15a of the outer jacket element 15 forms a flange 15d, configured to lean against the other end 14b of the elastic element 14. The elastic element 14 is sandwiched between the flange 15d and the shaft shoulder 13c. The inner wall of the other end 15b of the outer jacket element 15 is provided with two opposite bumps 15c, which are cylindrical bumps. Of course, in other implementation manners, the number of the bumps 15c may be one or more along an axial direction of the outer jacket element 15.

Figure 5:
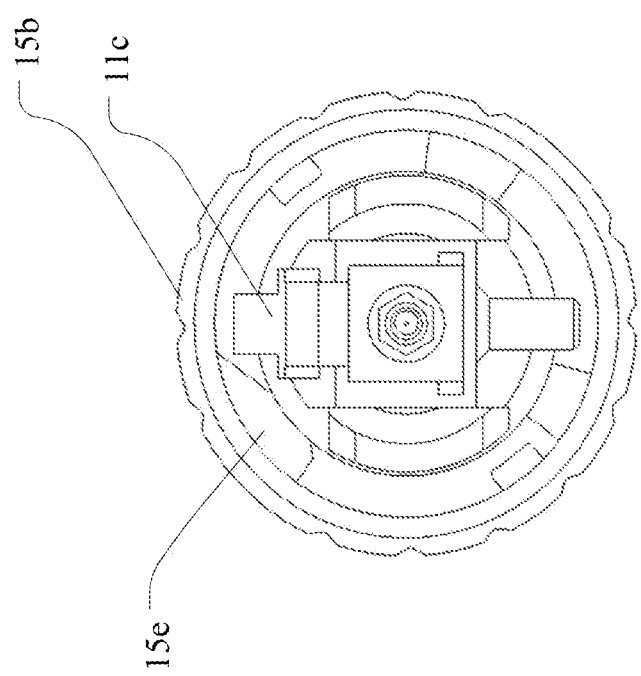
FIG. 5 is a schematic view of an end surface of the optical fiber connector assembly in FIG. 2.

The inner wall of the other end 15b of the outer jacket element 15 has a wedge block 15e (referring to FIG. 5) disposed along the axial direction of the outer jacket element 15, where the wedge block 15e is configured to press the buckling elastic piece 11c to achieve unlocking of the buckling elastic piece 11c. An outer surface of the other end 15b of the outer jacket element 15 has an arrow alignment identifier, configured to indicate a connected status and a loose status of the optical fiber connector 100. If the arrow on the outer jacket element 15 is aligned with the vertical line identified by "O" on the optical fiber adapter 20 (referring to FIG. 9), the optical fiber connector 100 is in the loose status. If the arrow on the outer jacket element 15 is aligned with the vertical line identified by "C" on the optical fiber adapter 20, the optical fiber connector 100 is in a locked status. An outer surface of the end 15a of the outer jacket element 15 has symmetrical flattened planes with vertical shallow trenches 15f in the planes to make the touch more sensible.

Figure 6:
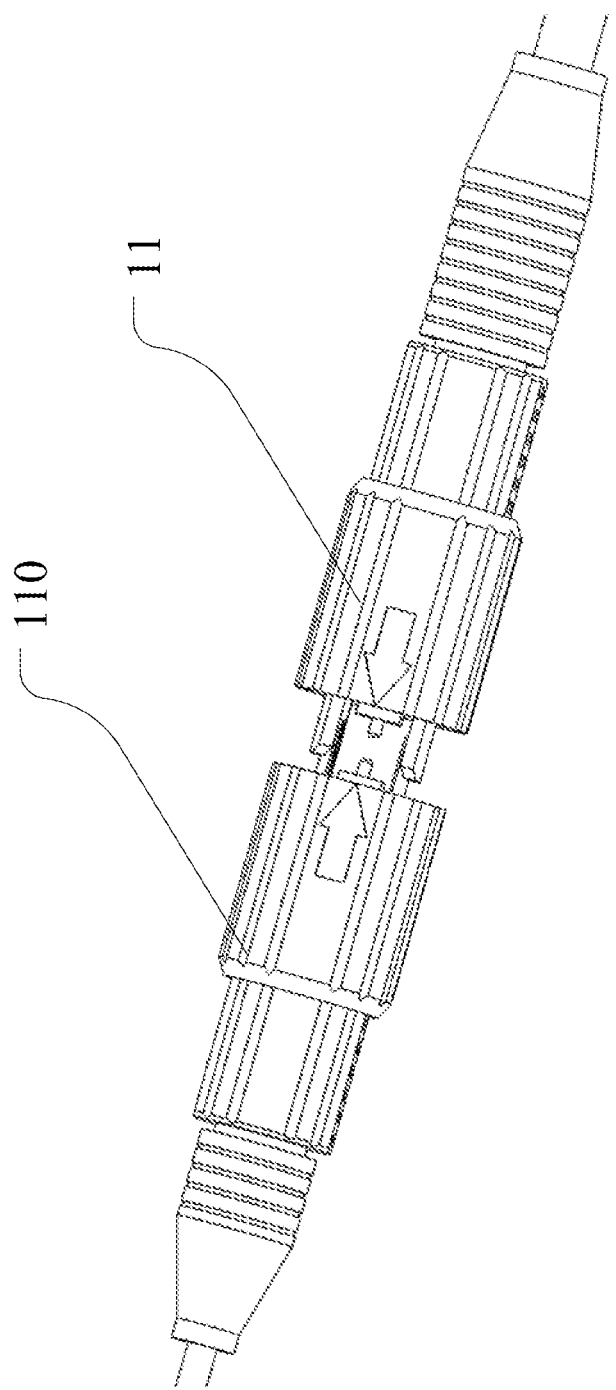
FIG. 6 is a schematic view showing a connection between two optical fiber sub-assemblies.
Figure 7:
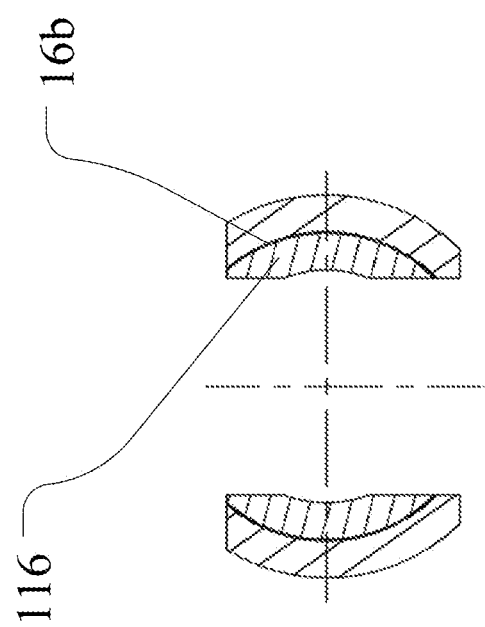
FIG. 7 is a schematic view of a protection key during the connection between two optical fiber sub-assemblies in FIG. 6.

The two protection keys 16 are disposed opposite to each other on the two sides of the ferrule 11. The protection keys 16 extend along an axial direction of the ferrule 11 and the end 11b of the ferrule 11 that is away from the inner jacket element 13 is retained between the two protection keys 16. The protection key 16 protrudes from the end 11b of the ferrule 11 to achieve protection of the ferrule and prevent an end surface of the ferrule 11 from being contaminated due to contact with other components when the optical fiber connector assembly 10 is inserted in or plugged out, or protect the ferrule 11 against a strike when the ferrule 11 falls down exceptionally. In this implementation manner, one end of the protection key 16 is fixed to a thimble 16a, where the thimble 16a is sleeved on the end 11b of the ferrule 11. An end of the protection key 16 is a rectangular piece with a stepped groove 16b on one end. The stepped groove 16b is configured to be sleeved on a protection key 116 of another optical fiber connector assembly 110. The protection key 116 of the optical fiber connector assembly 110 is a rectangular piece that has a smaller space and a ladder structure, therefore achieving interconnection between the two optical fiber sub-assemblies 10 and 110. During interconnection, the protection key 116 with a smaller space is retained in a stepped groove 16b of the protection key 16, therefore ensuring the end surfaces of the ferrules of the two optical fiber sub-assemblies 10 effectively contacting with each other (referring to FIG. 6 and FIG. 7). In this embodiment, sections of the two protection keys 16 are completely symmetrical, as shown in FIG. 7. Of course, in other implementation manners, sections of the two protection keys 16 may be not completely symmetrical.

The end 13b of the inner jacket element 13 is fixed to and sealed with the optical fiber 12 through a rubber heat shrinkable sleeve 5.

The rear retainer 17 is sleeved on the rubber heat shrinkable sleeve 5 and is fixed by using a retainer ring 4, to increase the tensile strength and air tightness of the optical fiber connector assembly 10. The rear retainer 17 may be fabricated first and then sleeved on the rubber heat shrinkable sleeve 5, and may also be poured at last in an integrated injection manner.

The optical fiber connector assembly 10 includes a connector assembly dust cap 30. The connector assembly dust cap 30 is dustproof and waterproof, and is configured to protect the ferrule. To prevent the connector assembly dust cap 30 from missing, the connector assembly dust cap 30 is tied to the optical fiber connector assembly 10 by using a lanyard 1. An end 31 of the connector assembly dust cap 30 is formed with a connector assembly receiving cavity 310, where the connector assembly receiving cavity 310 extends along an axial direction of the connector assembly dust cap 30 and the connector assembly receiving cavity 310 receives the ferrule 11 and the protection key 16. The connector assembly dust cap 30 has an O-shaped seal ring 2.

The connector assembly receiving cavity 310 is formed with a first notch 310a that matches the buckling elastic piece 11c. A periphery of the connector assembly dust cap 30 is formed with a first chute 31a, which matches the bump 15c. The first chute 31a is of a spiral shape, and extends from the end 31 of the connector assembly dust cap 30 along an axial direction of the connector assembly dust cap 30, and a rear end 31b of extension of the first chute 31a latches the bump 15c. In this implementation manner, the rear end 31b of extension of the first chute 31a is bent towards the end 31 of the connector assembly dust cap 30. The rear end 31b of extension of the first chute 31a is of an arc shape that matches the bump 15c.

Figure 8:
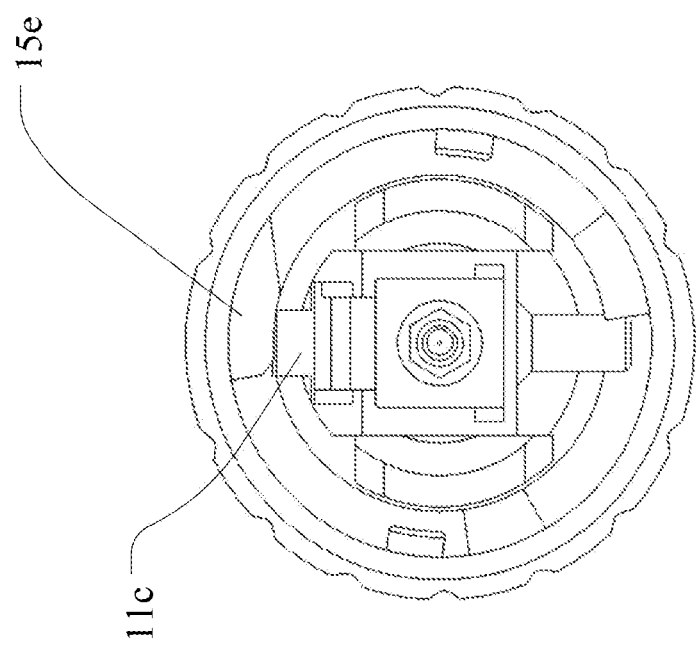
FIG. 8 is a schematic view showing that a buckling elastic piece of the optical fiber connector assembly in FIG. 2 is pressed.

When the connector assembly dust cap 30 is latched over the optical fiber connector assembly 10, if the outer jacket element 15 is rotated, the wedge block 15e presses the buckling elastic piece 11c lower (referring to FIG. 8), to insert the ferrule 11 and the protection key 16 into the connector assembly receiving cavity 310. The bump 15c of an optical fiber connector assembly 10d slides into the first chute 31a of the connector assembly dust cap 30. The outer jacket element 15 is rotated, so that the bump 15c slide to the rear end 31b of the first chute 31a. Meanwhile, the wedge block 15e is detached from the buckling elastic piece 11c and the buckling elastic piece 11c snaps in the first notch 310a, thereby achieving dual locking. Latching of the connector assembly dust cap 30 and the optical fiber connector assembly 10 is implemented through the foregoing operations. The elastic element 14 provides a pulling force for the outer jacket element 15, so that the bump 15c leans against the rear end 31b of the first chute 31a, thereby preventing a loose connection. During a disassembly process, the outer jacket element 15 is rotated in a direction reverse to that in the foregoing latching process, thereby achieving unlocking process.

Figure 9:
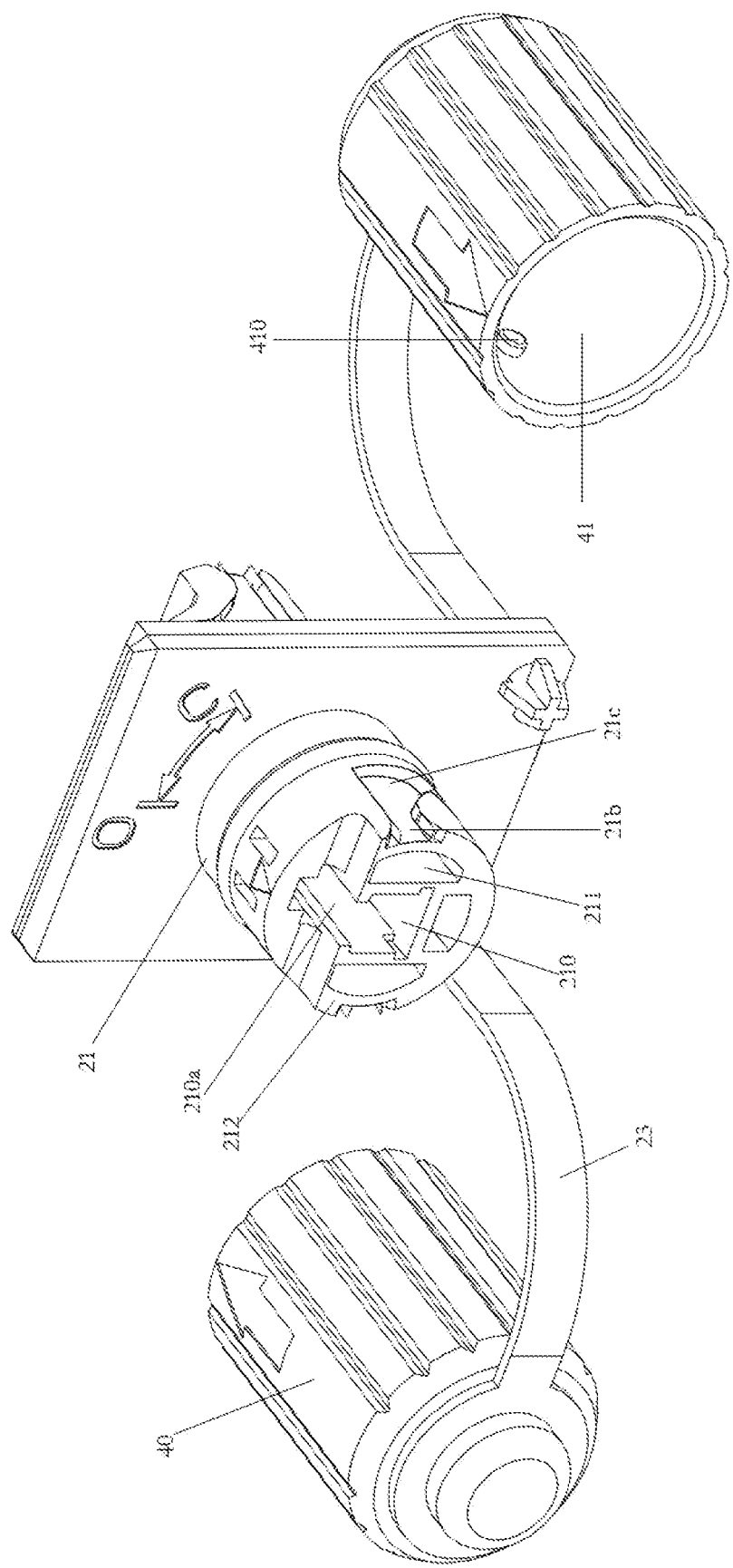
FIG. 9 is a schematic view of an optical fiber adapter of the optical fiber connector in FIG. 1.
Figure 10:
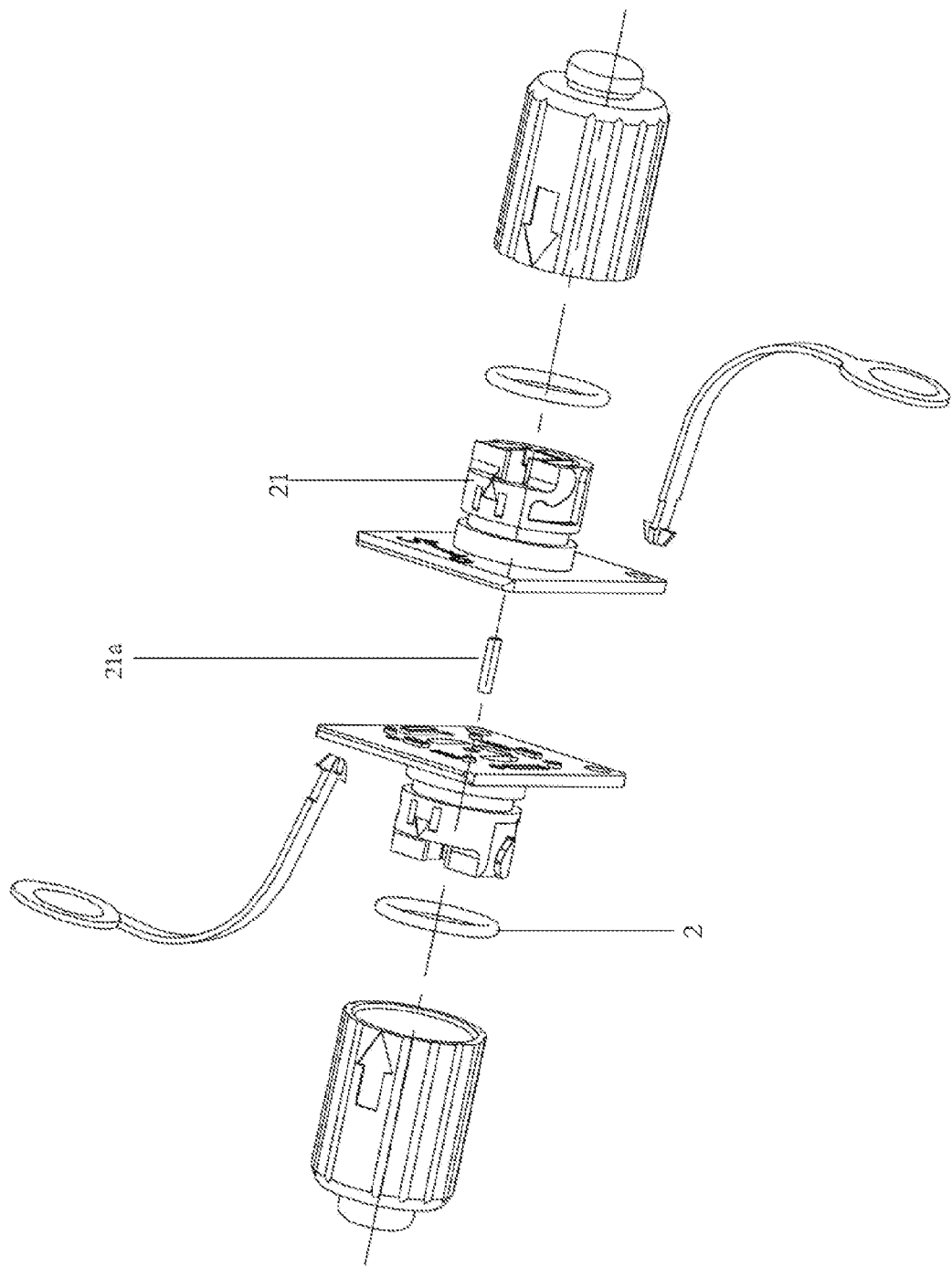
FIG. 10 is an exploded view of the optical fiber adapter in FIG. 9.

Referring to FIG. 9 and FIG. 10, the optical fiber adapter 20 includes two sockets 21, where the two sockets 21 and a ceramic sleeve 21a in the center of the optical fiber adapter 20 between the two sockets 21 may be welded together by using ultrasonic waves.

The socket 21 is formed with an optical fiber slot 210 and two protection key slots 211, where the optical fiber slot 210 and the two protection key slots 211 extend along an axial direction of the socket 21. The optical fiber slot 210 matches the ferrule 11, the protection key slots 211 match the protection keys 16, and the two protection key slots 211 are located on two sides of the optical fiber slot 210. In this implementation manner, the socket 21 is of a cylindrical shape. The optical fiber slot 210 is a square slot. Sections of the protection key 16 and the protection key slot 211 that matches the protection key 16 are both of a D shape with different top and bottom widths, which guides the insertion and prevents incorrect operation, such as reverse insertion or incorrect insertion. That is, when the optical fiber connector assembly 10 is inserted into the optical fiber adapter 20, if the D-shaped sections of the protection key 16 and the protection key slot 211 are not in the same direction, the optical fiber connector assembly 10 cannot be inserted into the optical fiber adapter 20.

The optical fiber slot 210 is formed with a second notch 210a, where the second notch 210a matches the buckling elastic piece 11c. A periphery of the socket 21 is formed with a second chute 21b, which is of a spiral shape. The second chute 21b extends from an end 212 of the socket 21 along the axial direction of the socket 21, and a rear end 21c of extension of the second chute 21b is bent towards the end 212 of the socket 21. The rear end 21c of extension of the second chute 21b latches the bump 15c. In this implementation manner, the second chute 21b and the first chute 31a are of the same shape.

When the optical fiber connector assembly 10 is inserted into the optical fiber adapter 20, the protection keys 16 and the ferrule 11 are inserted into the two protection key slots 211 and the optical fiber slot 210 respectively. The wedge block 15e presses the buckling elastic piece 11c lower. The bump 15c of the optical fiber connector assembly 10d slides into the second chute 21b of the optical fiber adapter 20. The outer jacket element 15 is rotated so that the bump 15c slides into the rear end 21c of the second chute 21b, thereby achieving locking. Meanwhile, the wedge block 15e is detached from the buckling elastic piece 11c and the buckling elastic piece 11c snaps in the second notch 210a, thereby achieving dual locking. A connection between the optical fiber connector assembly 10 and the optical fiber adapter 20 is implemented through the foregoing operations. During a disassembly process, the outer jacket element 15 is rotated in a direction reverse to that in the foregoing latching process, thereby implementing a reverse unlocking process.

The optical fiber adapter 20 includes an adapter dust cap 40. One end 41 of the adapter dust cap 40 is formed with an adapter receiving cavity 41 for receiving the optical fiber adapter 20. An inner wall of the adapter receiving cavity 41 is provided with a bump 410. The bump 410 is slideably connected in the second chute 21b. In this implementation manner, the inner wall of the adapter receiving cavity 41 is provided with two opposite cylindrical bumps 410. An outer surface of the end 41 of the adapter dust cap 40 has an arrow alignment identifier configured to indicate whether the adapter dust cap 40 is tightly locked. The adapter dust cap 40 has an O-shaped seal ring 2. The adapter dust cap 40 is tied to the optical fiber adapter 20 by using a lanyard 23 to prevent the adapter dust cap 40 from missing.

A connection process between the optical fiber adapter 20 and the adapter dust cap 40 is the same as the connection process of latching the connector assembly dust cap 30 over the optical fiber connector assembly 10.

The optical fiber connector provided in the present invention may be used as an outdoor connector to achieve plug and play. The optical fiber connector supports blind-mate, and the operation is convenient. The time taken to install and disassemble the optical fiber connector is only one-fifth of the time taken to install and disassemble a common thread connector.

Finally, it should be noted that the foregoing embodiments are merely intended for describing the technical solutions of the present invention rather than limiting the present invention. Although the present invention is described in detail with reference to the foregoing embodiments, a person of ordinary skill in the art should understand that they may still make modifications to the technical solutions described in the foregoing embodiments or make equivalent replacements to some technical features thereof, without departing from the spirit and scope of the technical solutions of the embodiments of the present invention.

What is claimed is:

1. An optical fiber connector assembly comprising:
a ferrule comprising a buckling elastic piece;
an optical fiber on which the ferrule is sleeved;
an inner jacket element sleeved on one end of the ferrule, wherein the buckling elastic piece is fixed to one end of the ferrule away from the inner jacket element and the buckling elastic piece extends towards the inner jacket element;
an elastic element, wherein one end of the elastic element leans against one end of the inner jacket element adjacent to the ferrule; and
an outer jacket element sleeved on the inner jacket element and the ferrule, wherein on end of the outer jacket element is slideably connected to the inner jacket element and leans against an other end of the elastic element, wherein the elastic element is configured to provide an elastic force to the outer jacket element in a direction away from the ferrule, wherein an inner wall of an other end of the outer jacket element is provided with a bump, wherein the optical fiber connector assembly comprises at least one protection key, and one end of the at least one protection key is provided with a stepped groove, and wherein the stepped groove is configured to be sleeved on a protection key of another optical fiber connector assembly.

2. The optical fiber connector assembly according to claim 1, wherein the inner wall of the other end of the outer jacket element is provided with two opposite bumps.

3. The optical fiber connector assembly according to claim 1, wherein the inner wall of the other end of the outer jacket element is provided with a plurality of bumps along an axial direction of the outer jacket element.

4. The optical fiber connector assembly according to claim 1, wherein the optical fiber connector assembly comprises two protection keys, wherein the two protection keys are disposed opposite to each other on two sides of the ferrule, wherein sections of the two protection keys are completely symmetrical and the sections of the protection keys are of a D shape with different top and bottom widths, and wherein the protection keys extend along an axial direction of the ferrule and one end of the ferrule away from the inner jacket element is retained between the two protection keys.

5. The optical fiber connector assembly according to claim 1, wherein the elastic element is a spring, and wherein the elastic element is sleeved on the inner jacket element.

6. The optical fiber connector assembly according to claim 5, wherein the bump is a cylindrical bump.

7. The optical fiber connector assembly according to claim 6, wherein the inner wall of the other end of the outer jacket element is provided with a wedge block disposed along an axial direction of the outer jacket element, and wherein the wedge block is configured to press the buckling elastic piece.

8. The optical fiber connector assembly according to claim 7, wherein the optical fiber connector assembly comprises two protection keys, wherein the two protection keys are disposed opposite to each other on two sides of the ferrule, wherein the optical fiber connector assembly comprises a connector assembly dust cap, wherein one end of the connector assembly dust cap is formed with a connector assembly retaining cavity and the connector assembly retaining cavity extends along an axial direction of the connector assembly dust cap; the connector assembly retaining cavity is formed with a first notch that matches the buckling elastic piece;
wherein the connector assembly retaining cavity receives the two protection keys and the ferrule, and
wherein a periphery of the connector assembly dust cap is formed with a first chute, wherein the first chute matches the bump, wherein the first chute is of a spiral shape, wherein the first chute extends from one end of the connector assembly dust cap along a axial direction of the connector assembly dust cap, and a rear end of extension of the first chute latches the bump.

9. An optical fiber connector comprising an optical fiber connector assembly and an optical fiber adapter that matches the optical fiber connector assembly, wherein the optical fiber connector assembly comprises:
a ferrule comprising a buckling elastic piece;
an optical fiber on which the ferrule is sleeved;
an inner jacket element, wherein the inner jacket element is sleeved on one end of the ferrule, wherein the buckling elastic piece is fixed to one end of the ferrule away from the inner jacket element and the buckling elastic piece extends towards the inner jacket element;
an elastic element, wherein one end of the elastic element leans against one end of the inner jacket element adjacent to the ferrule; and
an outer jacket element sleeved on the inner jacket element and the ferrule, wherein one end of the outer jacket element is slideably connected to the inner jacket element and leans against an other end of the elastic element, wherein the elastic element is configured to provide an elastic force to the outer jacket element in a direction away from the ferrule, wherein an inner wall of an other end of the outer jacket element is provided with a bump and a wedge block;
wherein the optical fiber adapter comprises a socket that is formed with an optical fiber slot and two protection key slots,
wherein the optical fiber slot and the two protection key slots extend along an axial direction of the socket, the optical fiber slot is formed with a notch that matches the buckling elastic piece, the two protection key slots are located on two sides of the optical fiber slot, and the optical fiber slot matches the ferrule,
wherein the optical fiber connector assembly further comprises two protection keys, wherein the protection key slots matches the two protection keys, wherein a periphery of the socket is formed with at least one chute, wherein the at least one chute matches the bump, wherein the at least one chute is of a spiral shape, wherein the at least one chute extends from one end of the socket along a axial direction of the socket, and a rear end of extension of the at least one chute latch the bump, and
wherein the wedge block is configured to press the buckling elastic piece to the notch when rotating the outer jacket element.

* * * * *